United States Patent [19]
Bara et al.

[11] Patent Number: 6,013,247
[45] Date of Patent: Jan. 11, 2000

[54] COMPOSITION FOR PROTECTING THE SKIN OR THE HAIR, CONTAINING NANOPIGMENTS AND A SOLID ELASTOMERIC POLYORGANOSILOXANE COMBINED WITH A FATTY PHASE

[75] Inventors: Isabelle Bara, Paris; Patricia Lemann, Chatillon, both of France

[73] Assignee: L'Oreal, Paris, France

[21] Appl. No.: 08/905,782

[22] Filed: Jul. 29, 1997

[30]    Foreign Application Priority Data

Jul. 29, 1996  [FR]   France ................................. 96 09525

[51] Int. Cl.⁷ .............................. A61K 7/42; A61K 31/74
[52] U.S. Cl. ............................... 424/59; 424/78.03
[58] Field of Search ..................... 424/59, 78.03

[56]         References Cited
             U.S. PATENT DOCUMENTS 4,621,029  11/1986  Kawaguchi ........................ 428/447

5,266,321  11/1993  Shukuzaki et al. ..................... 424/401

FOREIGN PATENT DOCUMENTS

| 0 271 925 | 6/1988 | European Pat. Off. . |
| 0 279 319 | 8/1988 | European Pat. Off. . |
| 0 456 459 | 11/1991 | European Pat. Off. . |
| 514067 A1 | 2/1992 | European Pat. Off. . |
| 518 773 A1 | 12/1992 | European Pat. Off. . |
| 669126 A1 | 5/1995 | European Pat. Off. . |

*Primary Examiner*—Raymond Henley, III
*Attorney, Agent, or Firm*—Oblon, Spivak, McClelland, Maier & Neustadt, P.C.

[57]               ABSTRACT

A composition for topical application containing nanopigments and a solid elastomeric polyorganosiloxane combined with a fatty phase, in order to improve the protection factor provided by the nanopigments and stabilize the composition.

18 Claims, No Drawings

COMPOSITION FOR PROTECTING THE SKIN OR THE HAIR, CONTAINING NANOPIGMENTS AND A SOLID ELASTOMERIC POLYORGANOSILOXANE COMBINED WITH A FATTY PHASE

BACKGROUND OF THE INVENTION

1. Field of the Invention

The present application relates to a composition for topical application containing nanopigments and a solid elastomeric polyorganosiloxane combined with a fatty phase, in order to improve the ultraviolet-radiation protection factor provided by the nanopigments. It also relates to the use of a solid elastomeric polyorganosiloxane combined with a fatty phase, in and/or for the manufacture of a composition for topical application to care for, treat or make up the skin or to care for the hair, containing nanopigments and having high screening properties. This composition may be applied to the human face, body and/or legs, as well as to the hands and the scalp.

2. Description of the Background

It is known that light rays with wavelengths of between 280 nm and 400 nm permit tanning of the human epidermis, and that rays with wavelengths more particularly between 280 nm and 320 nm, known as UVB rays, cause skin burns and erythema which may be harmful to the natural development of the tan; this UVB radiation should thus be screened out.

It is also known that UVA rays, with wavelengths of between 320 nm and 400 nm, which cause tanning of the skin, are liable to induce an adverse change in the latter, especially in the case of sensitive skin or of skin which is continually exposed to solar radiation. UVA rays cause in particular a loss of elasticity of the skin and the appearance of wrinkles, leading to premature skin ageing. They promote triggering of the erythema reaction or amplify this reaction in certain individuals and may even be the cause of phototoxic or photoallergic reactions. It is thus desirable also to screen out UVA radiation.

Different types of sunscreens for screening out UVA and UVB rays exist on the market: pigments and chemical screening agents. These sunscreens must be able to absorb or block out the harmful rays of the sun while at the same time remaining harmless to the user.

In this respect, metal oxide pigments are increasingly used in antisun products and day products, including make-up, given their properties of diffusing and reflecting UV radiation which gives them great value in terms of photoprotection: when used alone, they afford good protection against UV rays: when combined with organochemical screening agents, they allow highly photoprotective products to be produced. These pigments are preferably used in the form of nanopigments, the screening properties of which are well known.

Doctors are becoming increasingly aware that solar rays cause reactions which may lead to serious diseases such as skin cancer. Thus, it is increasingly sought to make antisun products and make-up or care products which have high protection factors.

For reasons of stability of these compositions and/or of toxicity on the skin or the mucosae, it is not always possible to use chemical screening agents or to increase their amounts in order to increase the protection factor of compositions containing nanopigments. Thus, the Applicants have looked into another way of increasing the protection factor of these compositions.

SUMMARY OF THE INVENTION

The Applicants have found, surprisingly, that by combining nanopigments with a solid elastomeric polyorganosiloxane combined with a fatty phase, the screening power of nanopigments is increased and that, accordingly, the protection factor (PF) of the composition containing them is markedly improved.

Thus, the subject of the invention is a composition for topical application containing nanopigments of at least one metal oxide, characterized in that it also contains a solid elastomeric polyorganosiloxane combined with a fatty phase, in order to improve the protection factor provided by the nanopigments.

DETAILED DESCRIPTION OF THE INVENTION

EP-A-545,002 describes cosmetic compositions containing a solid elastomeric polyorganosiloxane combined with a fatty phase, and which may contain pigments. However, that document does not describe the combination of such a polyorganosiloxane with nanopigments. In addition, it neither describes nor suggests that the polyorganosiloxane can increase in this way the protection from the sun provided by the nanopigments.

It is known that nanopigments have the drawback of being difficult to introduce into cosmetic or dermatological compositions on account of their small size. Indeed, the average size of the elementary particles of nanopigments ranges from 5 to 100 nm and preferably from 10 to 60 nm, which represents specific surfaces that are ten times larger than those of standard pigments.

Consequently, nanopigments are difficult to disperse. Moreover, nanopigments have a tendency to destabilize emulsions containing them and to agglomerate over time or when the composition containing them is spread onto the skin.

In addition to increasing the protection factor, the use of a solid elastomeric polyorganosiloxane according to the invention makes it possible to obtain a composition containing nanopigments which is stable and in which the nanopigments are fully dispersed, this good state of dispersion being maintained over time, both in the composition and after spreading onto the skin or the hair.

Thus, another subject of the invention is the use of a solid elastomeric polyorganosiloxane combined with a fatty phase in a composition for topical application containing nanopigments, in order to improve the stability of the said composition and/or to give the said composition an improved protection factor.

In addition, the solid elastomeric polyorganosiloxane according to the invention gives the composition better sensory qualities of spreading and allows a matt effect and waterproofing to be obtained.

The protection factor (PF) represents the screening power in the UVA region. This UVA protection factor is determined on the basis of the method of evaluating the immediate and persistent UVA-induced pigmentation (Persistent Pigment Darkening: PPD), described by Chardon et al. (Method for the UVA protection assessment of sunscreens based on residual immediate pigment darkening. 20th Annual Meeting of the American Society for Photobiology, Marco Island, Fla. (USA), Jun. 20–24, 1992).

The elastomeric polyorganosiloxanes combined with a fatty phase which are in accordance with the invention are generally partially or totally crosslinked and possibly of three-dimensional structure. When included in a fatty phase, they transform, depending on the level of fatty phase used, from a product with a spongy appearance, when they are used in the presence of low contents of fatty phase, into a homogeneous gel, in the presence of larger amounts of fatty phase.

The elastomeric polyorganosiloxanes combined with a fatty phase of the invention are generally in the form of a gel consisting of an elastomeric polyorganosiloxane combined with a fatty phase, included in at least one hydrocarbon oil and/or one silicone oil. They may be chosen in particular from the crosslinked polymers described in Application EP-A-0,295,886.

According to that application, they are obtained by addition reaction and crosslinking of at least:
(a) one polyorganosiloxane having at least two lower alkenyl groups per molecule;
(b) one polyorganosiloxane having at least two hydrogen atoms linked to a silicon atom per molecule; and
(c) one platinum-type catalyst.

Lower alkenyl groups may be, for example, vinyl, allyl or propenyl groups. Platinum-type catalyst may be, for example, chloroplatinic acid, chloroplatinic acid-complexes and carrier-supported platinumn.

The elastomeric polyorganosiloxanes combined with a fatty phase according to the invention may also be chosen from those described in patent U.S. Pat. No. 5,266,321.

According to that patent, they are chosen in particular from:
i) polyorgano-polysiloxanes comprising units $R_2SiO$ and $RSiO_{1.5}$ and optionally units $R_3SiO_{0.5}$ and/or $SiO_2$ in which the radicals R, independently of each other, denote a hydrogen, an alkyl such as methyl, ethyl or propyl, an aryl such as phenyl or tolyl, or an unsaturated aliphatic group such as vinyl, and in which the weight ratio of the units $R_2SiO$ to the units $RSiO_{1.5}$ ranges from 1/1 to 30/1;
ii) insoluble polyorganopolysiloxanes which can be swollen in silicone oil, obtained by addition of an organohydrogenopolysiloxane (1) and a polyorganosiloxane (2) having unsaturated aliphatic groups such that the amount of hydrogen or of unsaturated aliphatic groups in (1) and (2) respectively is between 1 and 20 mol % when the polyorganosiloxane is acyclic and between 1 and 50 mol % when the polyorganosiloxane is cyclic.

The fatty phase combined with the solid elastomeric polyorganosiloxane consists of at least one hydrocarbon oil and/or of at least one silicone oil.

The hydrocarbon oils used according to the invention in combination with the elastomeric polyorganosiloxane are chosen from oils of animal origin, oils of plant origin, synthetic oils such as hydrogenated isoparaffin, synthetic esters and ethers, and mixtures thereof.

The silicone oils used according to the invention in combination with the elastomeric polyorganosiloxane are preferably chosen from linear polysiloxanes which are liquid or pasty at room temperature, such as alkylpolysiloxanes, alkylphenylpolysiloxanes and alkylpolydimethylsiloxane, and cyclic polysiloxanes such as octamethylcyclopentasiloxane and decamethylcyclopentasiloxane; or mixtures thereof.

The polyorganosiloxane is preferably present in the elastomeric polyorganositoxane/fatty phase mixture in the form of a homogeneous gel, the polyorganosiloxane having a concentration ranging from 3 to 80% by weight.

The gel resulting from this combination and containing the nanopigments may be used as it is and constitute in itself a care or make-up composition. It may also be incorporated into a care, treatment or make-up composition.

In the compositions according to the invention, the elastomeric polyorganosiloxane is present in an amount ranging from 0.3 to 60% and preferably from 5 to 30% of the total weight of the composition.

According to the invention, the nanopigments may or may not be surface-treated and may be chosen in particular from nanopigments of titanium oxide (amorphous or crystallized in rutile and/or anatase form), of iron oxide, of zirconium oxide, of zinc oxide or of cerium oxide.

The treated nanopigments are pigments which have undergone one or more surface-treatments of chemical, electronic, mechanochemical and/or mechanical nature with compounds as described, for example, in Cosmetics & Toiletries, February 1990, Vol. 105, pp. 53–64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen, elastin), alkanolamines, silicon oxides, metal oxides, sodium hexametaphosphate, alumina or glycerol.

The treated nanopigments may more particularly be titanium oxides treated with:
silica and alumina, such as the products "Microtitanium Dioxide MT 500 SA" and "Microtitanium Dioxide MT 100 SA" from the company Tayca, and the products "Tioveil Fin", "Tioveil OPERATIONS MANAGER", "Tioveil MOTG" and "Tioveil IPM" from the company Tioxide,
alumina and aluminum stearate, such as the product "Microtitanium Dioxide MT 100 T" from the company Tayca,
alumina and aluminum laurate, such as the product "Microtitanium Dioxide MT 100 S" from the company Tayca,
iron oxides and iron stearate, such as the product "Microtitanium Dioxide MT 100 F" from the company Tayca,
silica, alumina and silicone, such as the products "Microtitanium Dioxide MT 100 SAS", "Microtitanium Dioxide MT 600 SAS" and "Microtitanium Dioxide MT 500 SAS" from the company Tayca,
sodium hexametaphosphate, such as the product "Microtitanium Dioxide MT 150 W" from the company Tayca,
octyltrimethoxysilane, such as the product "T-805" from the company Degussa,
alumina and stearic acid, such as the product "UVT-M 160" from the company Kemira,
alumina and glycerol, such as the product "UVT-M212". from the company Kemira,
alumina and silicone, such as the product "UVT-M262" from the company Kemira.

The untreated titanium oxides may be, for example, those sold by the company Tayca under the trade names "Microtitanium Dioxide MT 500 B" or "Microtitanium Dioxide MT 600 B".

The untreated zinc oxides may be, for example, those sold by the company Sumitomo under the name "Ultra Fine Zinc Oxide Powder" by the company Presperse under the name "Finex 25", by the company Ikeda under the name "MZO-25" or by the company Sunsmart under the name "Z-COTE". The treated zinc oxides may be, for example, those sold by the company Sunsmart under the name "Z-COTE HP 1".

The nanopigments may be introduced into the compositions according to the invention as they are or in the form of a pigmentary paste, that is to say mixed with a dispersing agent, as described, for example, in document GB-A-2,206,339.

The metal oxide nanopigments may be present in the compositions according to the invention in a proportion ranging from 0.5 to 30%, preferably from 2 to 20%, of the total weight of the composition.

According to a preferred embodiment of the invention, the compositions of the invention, which are preferably cosmetic or dermatological compositions, contain a physiologically acceptable medium, that is to say one which is compatible with the skin, the scalp and the hair, and may be used as compositions for protecting the human epidermis or the hair against ultraviolet rays, as antisun compositions or as make-up, treatment or care products for the skin.

The compositions obtained are easy to spread and provide different effects depending on the type of nanopigments used. Thus, compositions containing nanotitania provide a slight opalescent effect on the skin and lighten the complexion. Moreover, iron oxide nanopigments give a natural, radiant make-up.

The compositions of the invention may be in any pharmaceutical form normally used for topical application, such as solutions, aqueous or aqueous-alcoholic gels, emulsions, in particular oil-in-water or water-in-oil emulsions, and more particularly droplets of oil dispersed in spherules in an aqueous phase. These spherules may be polymer nanoparticles such as nanospheres and nanocapsules or, better still, lipid vesicles. The compositions of the invention may be in the form of a cream, an ointment, a lotion, a milk or a serum.

According to a preferred embodiment of the invention, the compositions are anhydrous.

The compositions of the invention may also contain any adjuvant conventionally used in the cosmetic or dermatological field, in the usual concentrations. These adjuvants are chosen in particular from gelling agents, preserving agents, opacifiers, emulsifiers, co-emulsifiers, neutralizing agents, fragrances and solubilizing or peptizing agents thereof, dyestuffs and fillers, as well as lipophilic or hydrophilic active agents and chemical screening agents. These adjuvants are present in amounts preferably ranging from 0.01 to 30% of the weight of the composition.

Obviously, these adjuvants must be of a nature and concentration such that they do not lower the protection factor of the composition and do not destabilize this composition.

In particular, organochemical UVA and/or UVB screening agents may be added to the compositions according to the invention, the organic UVA screening agents being added in order to complement the protective effect provided by the nanopigments and the UVB screening agents in order to avoid sunburn when users of this composition are exposed to solar rays.

The make-up products generally contain fillers. The term fillers is understood to refer to natural or synthetic materials whose main function is to modify the physicochemical (theological, mechanical, optical) and/or cosmetic properties of a composition. The fillers are colorless or more or less white in the dry state. They are virtually transparent when dispersed in a binder. Among the fillers, mention may be made of talc, which is a hydrated magnesium silicate, used in the form of particles which are generally smaller than 40 $\mu$m; talc possesses moisture-absorbing properties and is used especially because of its creamy feel. These fillers are present in amounts preferably ranging from 0.01 to 40% of the weight of the composition.

The compositions according to the invention allow good protection, and in particular good photoprotection, of the skin and/or the hair and consequently have an effect on the photoinduced ageing of the skin as well as on the wrinkles and/or fine lines on the skin which are induced by solar radiation.

Thus, the invention also relates to the cosmetic use of the composition as defined above for protecting the skin and/or the hair and/or for combating photoinduced ageing of the skin and/or for combating wrinkles and/or fine lines on the skin which are induced by solar radiation.

The invention also relates to the use of the composition as defined above for the manufacture of a dermatological composition intended to protect the skin and/or the hair and/or combat photoinduced ageing of the skin and/or combat wrinkles and/or fine lines on the skin which are induced by solar radiation.

The invention also relates to a cosmetic and/or dermatological process for the photoprotection of the skin and/or the hair, characterized in that an effective amount of the composition as defined above is applied to the skin and/or the hair.

Lastly, the subject of the invention is a cosmetic and/or dermatological process for combating photoinduced ageing and/or for combating wrinkles and/or fine lines on the skin which are induced by solar radiation, characterized in that an effective amount of the composition as defined above is applied to the skin.

The example which follows serves to illustrate the invention without, however, being limiting in nature. In this example, the composition is given as a % by weight.

Example: Anhydrous facial balm

| Phase A: | |
|---|---|
| Partially crosslinked polydimethylorgano-siloxane/polydimethylsiloxane 6 cst (sold under the name KSG 16 by the company Kose) | 20% |
| Cyclopentadimethylsiloxane | 28.95% |
| Modified hectorite (Miglyol gel B sold by the company Huls) (gelling agent) | 30% |
| Phase B: | |
| Nanotitanium oxide (microtitanium dioxide MT100 T sold by the company Tayca) | 10% |
| Hydrogenated isoparaffin (polysynlane sold by the company Nippon Oils Fats | 9% |
| Phase C: | |
| Talc | 6% |

Procedure:

Phases A and B are prepared separately. Phase A is homogenized at room temperature. In order to prepare phase B, the nanotitanium oxides are gradually sprinkled into the oil with stirring; stirring is continued for 30 minutes and the mixture is then ground. Phase B is added to phase A. The mixture is homogenized and phase C is sprinkled in.

The white balm obtained has a protection factor of about 14.4 and may be used on facial skin as a day cream or as a foundation for correcting imperfections in the complexion before applying make-up.

The anti-UVA protection afforded by this balm was compared with that obtained using water-in-oil (W/O) and oil-in-water (O/W) emulsions containing an identical amount of the same nanotitanias.

As shown above, the protection factors PF are determined according to the PPD method. The tests are carried out on the backs of individuals, on whom regions of skin with a surface area of about 7.5 $cm^2$ are delimited. The test product is only applied on certain regions. Fifteen minutes after applying the product, all the regions (those which have received the product and the others) are exposed to UVA produced by a 150 W xenon arc lamp fitted with WG 335 and UG 11 filters, delivering ultraviolet radiation doses of from 5 to 38 joules/$cm^2$, these doses being in a geometrical progression of 50%.

The minimum pigmenting dose (MPD), that is to say the dose which gives rise to the first pigmentation reaction that is unambiguously perceptible to the eye and homogeneous, is determined for a region protected with the test product (protected MPD) and for a region on which no product has been applied (unprotected MPD).

The protection factor is the ratio between protected MPD and unprotected MPD:

$$PF = \frac{\text{protected MPD}}{\text{unprotected MPD}}$$

The results were as follows:

| Composition | PF obtained |
| --- | --- |
| Example according to the invention | 18.34 |
| W/O emulsion | 17.06 |
| O/W emulsion | 13.48 |

These results show that addition of the elastomeric polyorganosiloxane according to the invention appreciably improves the protection factor provided by the nanopigments. The difference in protection factor between the W/O emulsion and the example according to the invention is significant.

The disclosure of priority France application 96-09525, filed Jul. 29, 1996, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A gel composition containing nanopigments of at least one metal oxide having an ultraviolet radiation protection factor property, and ultraviolet radiation protection factor improving amounts of a solid elastomeric polyorganosiloxane that is partially or totally crosslinked, and a fatty phase comprising a hydrocarbon oil or a silicone oil.

2. The composition according to claim 1, wherein the elastomeric polyorganosiloxane combined with a fatty phase is obtained by an addition reaction and crosslinking of at least:

(a) one polyorganosiloxane having at least two lower alkenyl groups per molecule;

(b) one polyorganosiloxane having at least two hydrogen atoms linked to a silicon atom per molecule; and (c) one platinum-type catalyst.

3. The composition according to claim 1, wherein the polyorganosiloxane is selected from the group consisting of:

i) polyorganopolysiloxanes comprising units $R_2SiO$ and $RSiO_{1.5}$ and optionally units $R_3SiO_{0.5}$ and/or $SiO_2$ in which the radicals R, independently of each other, are hydrogen, alkyl, alkyl, aryl or an unsaturated aliphatic group, and in which the weight ratio of the units $R_2SiO$ to the units $RSiO_{1.5}$ ranges from 1/1 to 30/1;

ii) insoluble polyorganopolysiloxanes which can be swollen in silicone oil, obtained by addition of an organohydrogenopolysiloxane (1) and a polyorganosiloxane (2) having unsaturated aliphatic groups such that the amount of hydrogen or of unsaturated aliphatic groups in (1) and (2) respectively is between 1 and 20 mol % when the polyorganosiloxane is acyclic and between 1 and 50 mol % when the polyorganosiloxane is cyclic.

4. The composition according to claim 1, wherein the hydrocarbon oils are selected from the group consisting of oils of animal origin, oils of plant origin, synthetic oils, synthetic esters and ethers, and mixtures thereof.

5. The composition according to claim 1, wherein the silicone oils are selected from the group consisting of linear polysiloxanes which are liquid or pasty at room temperature, cyclic polysiloxanes and mixtures thereof.

6. The composition according to claim 1, wherein the solid elastomeric polyorganosiloxane combined with a fatty phase is present in the form of a homogeneous gel, and the concentration of the polyorganosiloxane is from 3 to 80% by weight of the combination of said polyorganosiloxane and said fatty phase.

7. The composition according to claim 1, wherein the solid elastomeric polyorganosiloxane is present in an amount ranging from 0.3 to 60% of the total weight of the composition.

8. The composition according to claim 1, wherein the nanopigments comprise the elementary particles of from 10 to 60 nm in size.

9. The composition according to claim 1, wherein the nanopigments are selected from the group consisting titanium oxide, iron oxide, zirconium oxide, zinc oxide and cerium oxide.

10. The composition according claim 1, wherein the nanopigments are coated.

11. The composition according to claim 1, obtained by introducing the nanopigments in the form of a pigmentary paste.

12. The composition according claim 1, wherein the nanopigments are present in a proportion ranging from 0.5 to 30% of the total weight of the composition.

13. The composition according to claim 1, additionally containing at least one filler.

14. The composition according to claim 1, additionally containing at least one skin care or skin make up ingredient.

15. The composition according to claim 1, in anhydrous form.

16. A method for protecting the skin and/or the hair comprising applying an effective amount to the skin and/or hair of the composition of claim 1.

17. A method for combating photoinduced ageing of the skin and/or for combating wrinkles and/or fine lines on the skin which are induced by solar radiation comprising applying an effective amount to the skin of the composition of claim 1.

18. A method for improving the ultraviolet radiation protection factor and/or stability of a gel composition containing nanopigments having an ultraviolet radiation protection factor property, comprising adding to said composition a solid elastomeric polyorganosiloxane that is partially or totally crosslinked, and a fatty phase comprising a hydrocarbon oil or a silicone oil, in ultraviolet radiation protection factor improving amounts and/or stability improving amounts.

* * * * *